United States Patent [19]

Turner

[11] Patent Number: 5,455,164
[45] Date of Patent: * Oct. 3, 1995

[54] RUMINANT IMMORTALIZED MAMMARY EPITHELIAL CELL LINES

[75] Inventor: Jeffrey D. Turner, Hudson, Canada

[73] Assignee: McGill University, Quebec, Canada

[*] Notice: The portion of the term of this patent subsequent to Jul. 13, 2010 has been disclaimed.

[21] Appl. No.: 56,028

[22] Filed: Apr. 30, 1993

Related U.S. Application Data

[63] Continuation-in-part of Ser. No. 431,294, Nov. 3, 1989, Pat. No. 5,227,301.

[51] Int. Cl.$^6$ .............................. C12N 5/00; C12N 15/00
[52] U.S. Cl. ........................ 435/240.2; 435/172.3; 435/240.1; 435/240.21; 435/948; 935/70; 935/111
[58] Field of Search ........................ 435/240.2, 240.1, 435/240.21, 172.3, 69.1, 948; 935/70, 111

[56] References Cited

U.S. PATENT DOCUMENTS

| | | |
|---|---|---|
| 4,808,532 | 2/1989 | Stampfer . |
| 5,026,637 | 6/1991 | Soule et al. . |
| 5,227,301 | 7/1993 | Turner et al. ........................ 435/240.2 |

OTHER PUBLICATIONS

Romagnolo et al. (1), J. Dairy Science 75:293, abstract #P445 (1992) (Suppl. 1).
Romagnolo et al. (b), Mol. Endocrinol. 6(11):1774–1780 (1992).
R. S. Eisenstein et al., Molecular and Cellular Biology, 1988, vol. 8, pp. 3183–390.
D. Medina et al., Experimental Cell Research, 1987, vol. 172, pp. 192–203.
Bo Van Deurs et al., The Journal of Histochemistry and Cytochemistry, 1987, vol. 35, No. 4, pp. 461–469.
S. Yasumoto et al., Molecular and Cellular Biology, 1984, vol. 4, No. 4, pp. 712–721.
P. S. Jat et al., J. of Virology, 1986, vol. 59, No. 3, pp. 746–750.
K. G. Danielson et al., Proc. Natl. Acad. Sci. U.S.A., 1984, vol. 81, pp. 3756–3760.

*Primary Examiner*—Jasemine C. Chambers
*Attorney, Agent, or Firm*—Dressler, Goldsmith, Shore & Milnamow, Ltd.

[57] ABSTRACT

The present invention relates to a ruminant immortalized mammary epithelial cell line which has normal physiological responses in that it produces milk constituents which comprises α and β-casein and lactose. There is provided, using the cell line of the present invention a method in vitro studying lactation. There is provided a method of in vitro screening for gene expression of DNA constructs for transgenic ruminant animals. The cell line can be further used in a method for expressing foreign genes. One cell line of the present invention has been deposited at the ATCC under the accession number CRL10274.

5 Claims, 3 Drawing Sheets

+1 = APPROXIMATE SITES OF INITIATION OF TRANSCRIPTION
ATG = START CODON
▒ = LEADER SEQUENCE
▨ = MATURE PEPTIDE
105 bp = E-PEPTIDE
3' UTR; 271 bp = 3'-UNTRANSLATED REGION

RUMINANT IMMORTALIZED MAMMARY EPITHELIAL CELL LINES

This application is a continuation-in-part application of application Ser. No. 431,294 filed on Nov. 3, 1989, now U.S. Pat. No. 5,227,301, issued Jul. 13, 1993.

BACKGROUND OF THE INVENTION (a) Field of the Invention

The invention relates to ruminant immortalized mammary cell lines capable of expressing foreign genes, and wherein the mammary gland is the target organ for the gene expression.

(b) Description of Prior Art

Establishment of cell lines of mammary epithelial origin is critical for studies on the mechanism of action of lactogenic hormones and as a simple, biologically meaningful in vitro test system for recombinant DNA constructs destined for expression within the mammary glands of transgenic animals. Milk synthesis occurs within clusters of differentiated mammary epithelial cells and is under the strict control of lactogenic peptides and steroid hormones. Initiation of milk synthesis is thereby coordinated temporally with parturition. The molecular mechanisms by which hormones stimulate and maintain lactation are poorly understood. Post-transcriptional regulation appears to be of primary regulatory significance (Goyette, W. A. et al., Cell (1979) 17:1013; Eisenstein, R. S. and Rosen, J. M., Mol. Cell. Biol. (1988) 8:3183). In mice, prolactin increases the half-life of casein mRNA by some 17 to 25 fold while gene transcription increases by 2 to 4 fold (Goyette, W. A. et al. (1979) idem). Complimentary work with any agricultural dairy species is completely lacking.

Industrial production of proteins using the powerful biosynthetic capacity of the bovine mammary gland is an emerging technology. Mammary epithelial cells within the bovine udder can produce over a kilogram of protein daily. This complex milk protein contains many post-translational modifications. Transgenic animals in which foreign genes are expressed in the mammary gland, offer a method of producing heterologous proteins without the restrictions of prokaryotic fermentation. The major barrier to exploiting this concept are the inadequacies of germ line manipulation in farm animals. Problems include modest expression of transgenes, and poor tissue specific expression. A gene expression screening system, which could identify superior gene constructs prior to gene transfer, would improve transgenic animal production.

It would be highly desirable to have established mammary cell lines which demonstrate hormone responsiveness and enhanced secretory capacity. They would offer an unparalleled system to explore novel DNA constructs within the target organ, the mammary gland of livestock species. Large numbers of recombinant DNA constructs can be rapidly assessed at modest cost.

Established cell lines should be clonal and capable of either continuous proliferation or differentiation depending on the hormonal and extracellular matrix signals. A transformed phenotype showing growth in soft agar or tumorigenicity is not desirable. Despite considerable development, no single cell line derived from mammary epithelial presents these attributes. The murine COMMA-D cell line exhibits mammary-specific differentiation when exposed to the appropriate extracellular matrix (ECM) and lactogenic hormones (Eisenstein, R. S. and Rosen, J. M.(1988) idem). However, this cell line is heterogeneous being composed of at least 3 cell types of which only 10–20% are capable of casein synthesis. Subcloning COMMA parental lines leads to a loss of prolactin responsiveness (Medina, D. et al., Exp. Cell. Res. (1987) 172:192) or a loss of ECM requirements and protein secretion (Ball, R. K. et al., Embo. J. (1988) 7:2089).

Spontaneous bovine mammary epithelial cells (BMEC) in long term culture have been reported to differentiate (Schmid, E. et al., J. Cell. Biol. (1983) 96:37). However, lactose and casein secretion is absent or extremely low and not inducible with prolactin (our unpublished data).

A variety of established human breast carcinoma lines exist T97D, MCF-7 (Van Deurs, B. et al. J. Histochem. (1987) 35:461), but these appear to be transformed and show variable expression of differentiate phenotype such as polarity, tight functions and secretion of milk specific constituents.

It would be highly desirable to have a bovine immortalized mammary cell line which would have normal physiological responses and hence would not be transformed.

Such a cell line would provide one skilled in the art with an in vitro system to study lactation, a gene expression system to screen DNA constructs prior to gene transfer and with a method of expressing foreign genes.

It would be highly desirable to have ruminant immortalized mammary cell lines which would have normal physiological responses and which would be capable of expressing foreign genes, and wherein the mammary gland is the target organ for the gene expression.

SUMMARY OF THE INVENTION

Surprisingly and in accordance with the present invention, there is provided an immortalized ruminant mammary epithelial cell line prepared by the transfection of primary ruminant mammary epithelial cells with an immortalizing gene, said cell line having normal physiological responses such that, under hormonal stimulation, milk constituents comprising α- and β-casein and lactose are produced.

In accordance with the present invention, there is provided an immortalized ruminant mammary epithelial cell line, wherein said cell line is transfected with a suitable DNA expression vector to express a gene product wherein a gene is cloned into said vector.

The cell lines of the present invention are immortalized but not transformed, and hence, behave in a normal physiological way except for their immortal property.

The immortalized cell lines of the present invention are capable of differentiating and secreting foreign proteins in vitro and hormonal responsive and have a prolonged growth in culture as a monolayer.

The mammary cell lines of the present invention provide a method of studying in vitro lactation due to its normal physiological responses.

A bovine cell line in accordance with one embodiment of the present invention has been deposited at the American Type Culture Collection (ATCC, 12301 Parklawn Drive, Rockville, Md. 20852 U.S.A.) on Oct. 24, 1989 under the accession number ATCC CRL10274 This deposit is available to the public upon the grant of a patent to the assignee, McGill University, disclosing same. The deposit is also available as required by Foreign Patent laws in countries wherein counterpart applications are filed.

Such a bovine cell line provides a method of in vitro screening for gene expression in transgenic cows prior to gene transfer when the mammary gland is the target organ for expression. The testing of DNA constructs prior to gene transfer reduces tremendously the cost of genetic engineering.

In accordance with the present invention, there is also provided immortalized bovine cell lines derived from the ATCC CRL10274 as modified to produce proteins selected from the group consisting of β-galactosidase, insulin-like growth factor, large T antigen, aminoglycoside phosphotransferase and hygromycin B phosphotransferase.

Although the bovine cell line ATCC CRL10274 is a welcomed tool to study bovine lactation and other dairy cattle application, in accordance with the present invention there is also provided immortalized mammary epithelial cell lines of ruminant species.

In accordance with the present invention, the term "ruminant species" is intended to mean any mammal provided with a four-compartment stomach referred to as a rumen.

In accordance with the present invention, there is also provided a method for expressing foreign genes in vitro which comprises the steps of:

a) cloning a desired foreign gene into a suitable DNA expression vector;

b) transforming the immortalized cell line of claim 1 with the DNA vector of step a); and c) isolating the expressed gene product.

DETAILED DESCRIPTION OF THE INVENTION

I-MAC-T Cell line (ATCC CRL10274)

The hallmark of differentiated mammary epithelial cells is copious secretion of milk specific components regulated by lactogenic hormones. We describe an established clonal cell line produced from primary bovine mammary epithelial cells by transfection with SV-40 large-T-antigen referred to as "MAC-T" (Mammary Alveolar Cells-Large T antigen). Differentiation was induced by augmenting cell-to-cell interactions on a floating extracellular matrix in the presence of prolactin. The differentiated phenotype was characterized to include 1) increased abundance of β-casein mRNA; 2) increased number and size of indirect immunofluorescent casein secretory vesicles; 3) $\alpha_s$ and βcasein secretion; and 4) increased lactose secretion. The established cell line of the present invention will facilitate studies on the cell biology of the bovine or ruminant mammary gland and will provide an in vitro screening system for DNA constructs destined for genome manipulation where the mammary gland is the target organ for expression.

Cells

Primary mammary gland cells were obtained by aseptic biopsy from lactating Holstein cows at slaughter and dissociated as described by Burwen, S. J. and Pitelka, D. (Exp. Cell. Res. (1980) 126:249). Mammary tissue was minced, placed in a trypsinizing flask to which was added 1:10 (w/v) dissociation media (1×Hank's Buffered Saline solution, 11 mM glucose, 4% bovine serum albumin and collagenase 200 IU/ml) and rotated at 200 rpm for 60 min at 37° C. Single primary cells obtained by filtration through 150 um Nitex screens were washed with Dulbecco's phosphate buffered saline (DPBS) and grown in Dulbecco's Modified Eagles Media (DMEM), 20% fetal calf serum (FCS), 5 µg/ml insulin, 1 µg/ml hydrocortisone, 100 IU/ml penicillin and 100 µg/ml streptomycin on tissue culture plastic with 5% $CO_2$ and 100% humidity at 37° C.

Prior to transfection, cells were dilution cloned and colonies arising from single cells with epithelial morphology were selected. These cells were sensitive to Geneticin® (G418 sulfate) such that 200 µg/ml resulted in 100% mortality.

Bovine mammary epithelial cells of the hormone-adapted BMEC⁺H clonal cell line were obtained from W. W. Franke (German Cancer Research Center, Heidelberg, F. R. G.). These cells were used as a positive control for immunohistochemical identification of epithelial cells and as a cell line for comparison of synthetic capability. Cells were grown in DMEM supplemented with 20% FCS, insulin, hydrocortisone and prolactin (1 µg/ml) on plastic (Schmid, E. et al. (1983) idem). Synthetic and secretory capacity of BMEC cells was assessed on floating collagen gels in the same way as our experimental mammary cell lines.

The P160 cell line was a v-abl transformed NIH 3T3 cell line obtained from J. C. Bell (University of Ottawa, Canada). They were grown in complete media; removed with trypsin, washed twice in $Ca^{++}$ free phosphate-buffered saline and $5 \times 10^5$ cells/100 µl injected into nude mice to serve as a positive control for the tumorigenicity assay.

DNA Transfection

Transfections were undertaken with adherent cells ($1.3 \times 10^5/cm^2$) using 10 µg pBAPSV40TtsA58 and 10 µg pSV2-neo per $1 \times 10^7$ cells by the calcium phosphate procedure of Graham, F. L. and van der Eb, A. J. (Virol. (1973) 52:456). After 4 h of transfection, the cells were washed once with DPBS and glycerol shocked for 2 min, washed with DPBS and complete media added for 24 h. Cells were then trypsinized and plated in 6 well multiplates ($5.2 \times 10^3$ cells/$cm^2$) in complete media with 400 µg/ml Geneticin®. Transfection efficiency averaged $6.5 \times 10^5$ cells. Surviving colonies were cloned by dilution and yielded 414 clones of which 250 were expanded and frozen.

Expression of the SV-40 large-T-antigen was directed from the plasmid pBAPSV40TtsA58 obtained from L. Chalifour, Biotechnology Research Institute (Montréal, Canada). This plasmid includes a 4.0 kb human β-actin promoter and a 0.75 kb SV-40 polyadenylation sequence and a 2.6 kb Bam HI fragment of SV-40 large-T-antigen (Jat, P. S. and Sharp, P. A. Mol. Cell. Biol. (1989) 9:1672). The pSV2-neo plasmid (Southern, P. J. and Berg, P., J. Mol. Appl. Gen. (1982) 1:327) was provided by G. Matlashewski (McGill University, Montréal) and conferred antibiotic resistance to Geneticin®.

This bovine immortalized mammary cell line has been deposited at the ATCC under the accession number CRL10274 and is designated as the MAC-T cell line.

Hormone-responsiveness to prolactin

Cloned cells with good growth characteristics were evaluated with regard to their hormone responsiveness to prolactin. Parameters evaluated included 1) intracellular casein accumulation by immunohistochemistry; 2) casein secretion by Western blotting; 3) β-casein mRNA abundance by Northern blotting; and 4) lactose secretion using an enzymatic assay. Cells were plated at high density ($9 \times 10^4$–$1.8 \times 10^5$ cells/$cm^2$) on calf tail collagen gels prepared as per Emerman, J. T. and Pitelka, D., IN VITRO (1977) 13:316). After 12 to 14 hours, dead cells were removed with two DPBS washes and media (DMEM, 5 μg/ml insulin and 1 μg/ml hydrocortisone and 2.5% FCS) supplemented with 5 μg/ml prolactin (USDA-6PRL-B-I) added and the gels were then released to float in this media. Aliquots of media were removed at 24, 36 and 48 h and 72 h after prolactin addition, and analyzed for lactose and casein content.

Lactose concentrations in media was measured using commercially available methods (Boehringer-Mannheim GmbH) with the following modifications: corrections were made for the presence of phenol red in media samples and 20 μl of a standard lactose solution (0.503 g/l) was used to spike each sample into the linear range of the standard curve.

Evaluation of α and β-casein within the media was evaluated by Western immunoblotting techniques and within cells by immunofluorescent cytochemistry. Proteins within the media were separated using SDS-PAGE, through 4% stacking gel and 10% separating cell (Laemmli, U.K., Nature (1970) 277:680). Gels were transferred by electroblotting to nitrocellulose filters (70 V, 3 h, 4° C.) and washed briefly in $H_2O$ then 20 mM Tris pH 7.5, 500 mM NaCl (TBS), blocked with 3% gelatin in TBS for 60 min then washed twice in TBS with 0.05% Tween 20® (TTBS). Rabbit anti-bovine antibodies to α and β-casein were diluted (1:2000) and incubated overnight in TTBS plus 1% gelatin. After two TBS washes, the filter was transferred to the second antibody goat anti-rabbit IgG conjugated to alkaline phosphatase (1:2000) for 60 min. Filters were washed twice with TTBS then TBS to remove Tween-20® and developed as recommended by Bio-Rad.

Total cellular RNA was extracted from cells grown on plastic tissue culture dishes and on collagen gels using the procedure of Towle, H. C. et al., Biochemistry (1980) 19:579). The integrity of each sample was verified by gel electrophoresis and the quantity determined spectrophotometrically. Northern blots were performed after capillary transfer of glyoxylated total RNA from a 1.5% agarose gel onto Zetaprobe® membrane (Bio-Rad). Bovine b-casein cDNA (Pst 1, 11506 bp, J. P. Mercier, INRA France) and bovine β-actin cDNA (Degen, J. L. et al. J. Biol. Chem. (1983) 258:12153) were labelled by oligo-labelling, denatured and used as hybridization probes.

Immunohistochemistry

Immunohistochemistry was used to 1) identify MAC-T cell lineage and 2) define prolactin effects on intracellular casein levels. Monoclonal antibodies (MAb) which react with cytokeratin (Jahn, L. et al., Differentiation (1987) 36:234; type II, subfamily No 1-8) and vimentin (Jahn, L. et al. (1987) idem) were used to characterize cell type as epithelial or stromal, respectively. When cells were grown on eight well chamber slides (plastic substrata), fixation and staining could be completed directly using manufacturers recommendations. Cells on collagen were briefly treated with collagenase and then plated on plastic for 30 min prior to staining. Immunofluorescent localization of the primary antibody was accomplished using a second antibody, goat anti-mouse Ig-FITC conjugate. Positive biological control for cytokeratin staining were the BMGE cells, which show a characteristic pattern (Schmid, E. et al. (1983) idem). Incubation of cells with FITC-goat anti-mouse IgG alone failed to result in cell staining.

Samples were directly visualized with a Jenalumar microscope, at 400× magnification, equipped with epifluorescence optics and appropriate excitory and barrier filters for FITC.

Antibodies directed toward bovine casein were used to assess whether exogenous prolactin would increase the casein content within MAC-T cells. Caseins ($\alpha_s$, and β) were purified by DEAE-cellulose chromatography from acid precipitated casein (Davies, D. T. and Law, A. J. M., J. Dairy Sci.(1977) 44:213), then emulsified with an equal volume of complete Freund's adjuvent and one ml (1 mg protein) injected intradermally into male New Zealand White rabbits (Charles River, Inc.). Booster injections of incomplete Freund's adjuvant were given monthly for two months. Serum was discomplemented by incubation at 56° C. for 30 min then aliquots frozen. Antibodies were diluted 1:5 in phosphate buffered saline (PBS) before use.

Secondary antibody, a goat anti-rabbit Ig-FITC (Boehringer-Mannheim GmbH) was used to locate casein containing vesicles within cells. Differentiated cells on collagen were briefly dissociated with mild collagenase treatment, and allowed to adhere in chambers slides, after which they were fixed and examined for immunologically reactive material.

Establishment characteristics

Tumorigenic potential, growth on soft agar and the presence of large-T-antigen were used to evaluate the nature of MAC-T cells. Tumorigenicity was evaluated by injecting $5 \times 10^6$ cells/100 μl DPBS subcutaneously into 28–40 day-old Nu/Nu CD-1 homozygous mice (Charles River Inc.). As a positive control P160 cells were also injected ($5 \times 10^5$ cells/ 100 μl ) at a different site. Mice were palpated for the presence of tumors after 8 weeks. Growth in soft agar was evaluated by placing 600 cell/ml on 0.3% agarose in complete media. Any colonies present after 16 days were counted.

Monoclonal antibodies to SV-40 large-T-antigen were provided by G. Matlashewski. These MAb were used at a dilution of 1:1 using the aforementioned methods with MAC-T cells attached to plastic and growing.

The MAC-T cells can exist in either a proliferarive or in a differentiated phenotype depending on exogenous hormones and extracellular matrix.

Concerning growth characteristics, when MAC-T cells are grown on tissue culture plastic, they show a doubling time of ~17 h and reach confluency at $4.2 \times 10^5$ cells/cm$^2$. These cells show contact inhibition and do not overgrow, but form a uniform pavement of closely associated cells. Conversely, when plated at half confluency on floating collagen gels in the presence of prolactin, cell growth expressed as total DNA concentration remains unchanged over 5 days. Difficulties in quantitatively removing cells from collagen gels was the reason for using DNA content as an indirect measure of cell number.

Phase contrast microscopy illustrated that MAC-T cells have characteristic epithelial morphology, growing in monolayers similar to those formed by primary epithelial cultures. Evidence of epithelial cell lineage was the characteristic array of cytoskeletal proteins, namely intermediate filaments which are clearly defined by indirect immunofluorescence with MAb's recognizing cytokeratin. The fluorescent pattern was very similar to those for the BMGE cells, a spontaneous established cell line of bovine or ruminant mammary gland origin (Schmid, E. et al. (1983) idem). Omission of the primary antibody abolished the immunofluorescent pattern. The absence of significant vimentin signal located within MAC-T cells indicated that they are not contaminated with fibroblasts or adipocytes. This was not surprising as the MAC-T cells are clonal in origin.

Nature of Establishment

The best evidence of establishment is longterm growth in culture without senescence or crisis. The MAC-T cells are currently >450 passages, which represents continuous culture for more than three year. In contrast, the primary cultures typically enter crisis between 20–50 passages. The extended growth of MAC-T cells appears to reflect establishment rather than oncogenic transformation. MAC-T cells are uniformly non-tumorigenic 0/7 when injected into immunodeficient mice. This result appears to be a true negative, as P160 cells initiated prompt tumor growth within control animals. The growth habit of the cells also argues for establishment as opposed to transformation. MAC-T cells do not overgrow or form foci and have an obligatory requirement for fetal calf serum mitogens, at a level of 5% supplementation. These cells are anchorage dependent as they do not grow on soft agar.

Transfection with SV-40 large-T expressing plasmids appears to be responsible for maintaining the established phenotype. Southern analysis confirms the presence of the SV-40 large-T antigen within the genome of the MAC-T cells. Expression of large-T antigen gene assessed by indirect immunofluorescence, indicated a low level constitutive expression. The low levels of SV-40 large-T antigen are sufficient to immortalize the cells but do not prevent differentiation when prolactin and extracellular matrix are present. Although the pBAPSV40TtsA58 plasmid has been shown to regulate cell proliferation in a temperature dependent way when integrated into the genomes of other cell types, MAC-T cells did not demonstrate fluctuations in large-T signal or growth rate when grown at 33° or 39.5° C.

MAC-T cell characteristics

The MAC-T cell line of the present invention is hormone-responsive. The choice of bovine mammary gland as a starting point is obvious. The diary industry relies on milk produced from a single epithelial cell type, without having an established cell line as an in vitro model. This discussion will focus on characterization of the MAC-T cell line including the nature of cell establishment and morphology, and growth characteristics and the differentiation potential, and prolactin sensitivity.

Establishment of MAC-T cells appears to be the result of constitutive low level expression of the SV-40 large-T antigen. This gene was located within the MAC-T genome and MAb's detect large-T antigen protein within the cells. Large-T antigen has previously been extensively used to establish primary rodent fibroblasts (Jat, P. S. and Sharp, P. A. (1989) idem; Rassoulzadegan, M. et al., PNAS (1983) 80:4354). The presence of the large-T antigen appears essential for maintenance of the transformed phenotype.

The MAC-T cells are immortalized and not transformed. MAC-T cells demonstrate topoinhibition, even at confluency. Cells within the monolayer are closely opposed and maintain cytoskeletal contact via desmosomes. MAC-T cells are anchorage dependent as shown by the absence of growth on soft agar. MAC-T cells do not initiate tumors in immunodeficient mice. These features are consistent with an immortalized cell line.

MAC-T cells exist as two phenotypes which are controlled by exogenous hormones and extracellular matrix. When grown on plastic substrata in the absence of prolactin, the cells divide rapidly and reach confluency at high cell densities. Today, these cells were >450 passages, which is the best evidence that this is in fact an established line. These growth properties are indispensable for experimentation involving large numbers of cells or transfection where a few positive clones must be grown-up. The second phenotype resembles a differentiated mammary epithelial. When plated on type I collagen in the presence of prolactin, MAC-T cells cease their mitotic activity and began synthesis and secretion of milk specific components.

II-Modified MAC-T cell lines

The MAC-T cell line (ATCC CRL10274) may be modified with a variety of eukaryotic expression vectors containing various foreign genes to be expressed. Such eukaryotic expression vectors may be selected from the group consisting of, but not limited to, pXTI, pSG5 and pOG44/45 sold by Stratagene Cloning Systems (11099 North Torrey Pines Road, La Jolla, Calif., U.S.A. 92037) under respective catalogue No. 214201, 216201 and 218405. The following eukaryotic expression vectors may also be used pSVK3 (catalogue No. 27-4511-01), pBPV (catalogue No. 27-4390-01), pMSG (catalogue No. 27-4506-01), pMSG-CAT (catalogue No. 27-4505-01), pSVL-SV40 (catalogue No. 27-4509-01), pCH110 (catalogue No. 27-4508-01) sold by Pharmacia (Baie d'Urfé, Qc, Canada).

Such foreign genes which may be transfected in the modified MAC-T cell lines via any eukaryotic expression vectors may be coding for, for example, human neuropeptide Y, yeast peroxisomal catalase, flounder antifreeze protein, human ferritin and human tissue plasminogen activator.

Examples of recombinant DNA expression vectors (constructs) in accordance with the present invention were described in various papers of the ICSU Short Reports (Proceedings of the 1988 Miami Bio/Technology Winter Symposium, IRL Press, Oxford, Washington, D.C. ISBN 1-85221-054-0), the teachings of which are incorporated herein by reference.

The proteins expressed, as gene products, by the modified MAC-T cell line may be, for example, human neuropeptide Y, yeast peroxisomal catalase, flounder antifreeze protein, human ferritin, human tissue plasminogen activator, β-galactosidase, insulin-like growth factor, large T antigen, aminoglycoside phosphotransferase and hygromycin B phosphotransferase.

III-Ruminant cell lines

The mammary gland is dependent on hormones for all aspects of its growth and function. It is a target tissue for many different hormones which act synergistically and, although such hormonal synergisms are by no means uncommon, those relating to the mammary gland are particularly complex. This regulation is necessary to achieve a fully functioning gland at only well-defined periods in the reproductive cycle, to coincide with the birth and subsequent nurturing of the young. Detailed studies of the mammary gland are confined to relatively few species and even in well-known and economically important mammals, like the dairy cow, our knowledge is still very incomplete.

Milk yield is dependent on the number of secretory cells in the mammary gland and the rate of milk synthesis by individual cells. The relative proportions of supporting connective tissue cells (or stroma) to epithelial cells (including ductal, secretory and myoepithelial cells, known together as 'mammary parenchyma') varies at different states in development. For this reason, and because mammary growth involves not just an increase in epithelial cell number but also an ordered pattern of branching morphogenesis, it is best described by a combination of biochemical and histological measures.

The secretory cells developed in the mammary gland during pregnancy also acquire the capacity to make milk, that is, become terminally differentiated. The time in pregnancy when secretory activity can first be detected varies between species. Appreciable synthesis of lactose occurs soon after mid-pregnancy in the goat and rabbit, but not until the day before delivery in the rat.

McClymont (Aust. J. Agric. Res. (1951) 2:158–180) first clearly demonstrated that acetate is a major metabolic substrate of the bovine mammary gland. Arteriovenous differences of blood acetate across the mammary gland were found to be closely correlated with arterial concentration and extraction rates of 40–80% were reported.

Folley and French (Biochem. J. (1950) 46:465–473) incubated mammary slices from lactating rats, rabbits, sheep and cows with acetate as the sole substrate. Ruminant mammary tissue respired actively and exhibited a respiratory quotient (RQ) above 1.0, but the non-ruminant tissue was less metabolically active, with an RQ<1.0, suggesting that ruminant tissue, but not non-ruminant tissue, could synthesize fat when acetate was the only available substrate.

Extrapolation of data across species has long been sought as a method to defray costs and enable testing, especially with regard to human research. Much data have been presented demonstrating subtle or distinct differences in mammary growth between species. Differences have included endogenous serum hormone levels, mammary gland responses to various mitogens, in vitro mammary epithelium responses to mitogens, differences in prepubertal, estrous cycling, or gestational growth, receptor levels and responsiveness of receptors.

Ruminant species may be used to produce immortalized cell lines in accordance with the present invention. The preferred ruminant species in accordance with the present invention are cow, sheep, goat and water buffalo.

In accordance with the present invention, there is provided a variety of immortalizing genes could be used in transforming ruminant cell lines for immortalization. The immortalizing genes which may be used in accordance with the present invention may be selected from the group consisting of, but not limited to, large T antigens of SV40 and of polyomavirus; adenovirus oncogenes, such as E1A and E1B; papillomavirus oncogenes, such as E6; nuclear oncogenes, such as myc, fos, erbA, jun and myb; among others. Other immortalizing genes may be used in accordance with the present invention, such as the genes disclosed in "Oncogenes and the Molecular Origins of Cancer" (Cold Spring Harbor Laboratory Press, Edited by Robert A. Weinberg, 1989), the teachings of which is hereby incorporated by reference.

The present invention will be more readily understood by referring to the following examples which are given to illustrate the invention rather than to limit its scope.

Example I

STUDY OF in vitro LACTATION

Prolactin and Extracellular Matrix Effect MAC-T cells (ATCC accession number CRL10274)

As lactose and casein proteins are not found in media or serum supplements, their presence in conditioned media is indicative of secretory capacity of differentiated mammary epithelial cells.

Beta-casein mRNA abundance within MAC-T cells responds to both exogenous prolactin and culture on floating collagen gels. MAC-T cells grown on plastic substrata without prolactin show very low levels of β-casein mRNA. Prolonged exposures are required to obtain autoradiographic signals. Attachment to floating collagen gels increases β-casein mRNA abundance by 24 h, initiating a higher steady state level. Exogenous prolactin and collagen leads to an augmented β-casein mRNA abundance, by 48 h. Constant β-actin signal confirms equal loading of total RNA in each electrophoretic lane.

Secretion of α and β-casein protein followed a temporal pattern consistent with that observed at the mRNA level. Western blot analysis shows that prolactin causes a strong stimulation of α and β-casein secretion by MAC-T cells on collagen by 48 h. Reflective densitometry gives an approximate 3-fold increase in β-casein secretion at this time. The concentration of β-casein was approximately 250 to 500 $\mu g/1\times10^7$ cells/24 h of conditioned media. In the absence of prolactin, casein secretion was lower and constant. Casein secretion is below the limits of detection when MAC-T cells are grown on plastic substrata without prolactin supplementation.

Figure 1A:
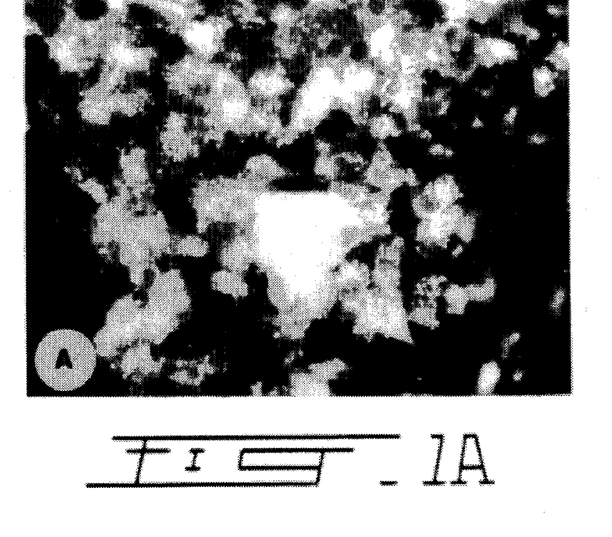
FIGS. 1A–1C show an indirect immunofluorescent visualization of $\alpha_s$ and β-casein with prolactin (A) without prolactin (B) and without casein specific primary antibody (C)
Figure 1B:
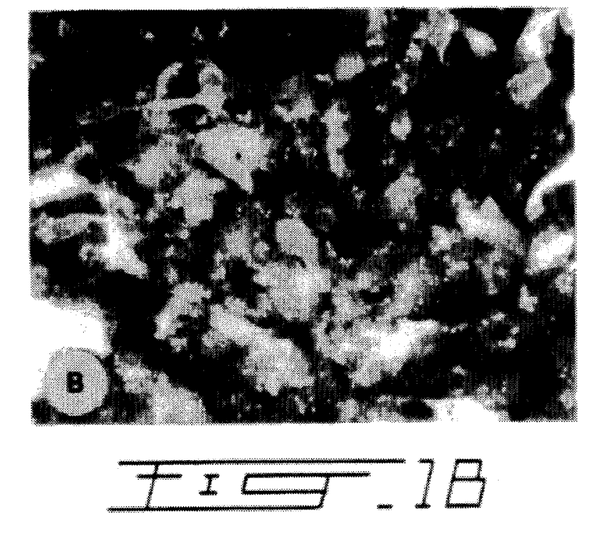
Figure 1C:
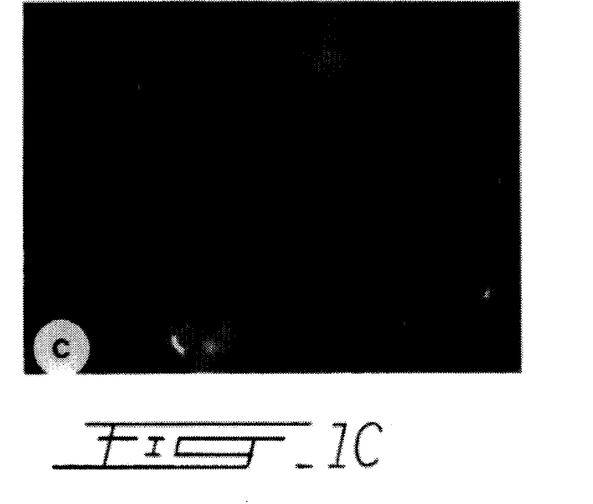

Immunological localization of α and β-casein produced a graphic demonstration of prolactin effects on intracellular casein content (FIG. 1). MAC-T cells exposed to prolactin (A) for 48 h were congested with numerous immunoreactive secretory vesicles. In properly oriented cells, the polarity of these granules with respect to the nucleus is evident. When MAC-T cells were grown on collagen without prolactin, the number of granules was reduced but not completely so (B). The absence of immunofluorescent staining of cells in the absence of primary antibody (C) indicated that these granules were casein-like. Prolactin in conjunction with a floating collagen gel led to the secretion of lactose and caseins. Lactose secretion as measured by lactose accumulation in the media ranged between 2 to 8 nmol/μg DNA/24 h. After 48 h on collagen, lactose secretion leveled off irrespective of prolactin stimulation. Prolactin did not appear to increase the maximum rate at which the MAC-T cells could secrete lactose but did allow for more accumulation within the media.

Secretory Functions

Two major constituents of milk are casein proteins and the disaccharide, lactose. As neither are found in culture media or serum supplements, their presence in conditioned media is indicative of secretory capacity of differentiated mammary epithelial cells. Casein gene expression and secretion of casein protein are regulated in MAC-T cells by a combination of extracellular matrix and hormonal signals. Concerning extracellular matrix, culturing MAC-T cells on plastic substrata prevented differentiation as defined biochemically. Beta-casein mRNA abundance was very low and α and β-casein secretion was not detectable. Whereas, culture on floating collagen gels produced dramatic increases in β-casein gene expression which began within 24 h and persisted for at least 3 days. Increases in casein secretion followed the rise in mRNA abundance. Sensitivity to substrata is consistent with other mammary epithelial cell lines and primary cells. COMMA-D cells increase casein mRNA abundance on floating collagen gels (Medina, D. et al. (1987) idem; Eisenstein, R. S. and Rosen, J. M. (1988) idem). Similarly primary mouse mammary cells (Emerman et al. 1977) and COMMA-D cells (Danielson, K. G. et al., PNAS (1989) 81:3756) showed an obligatory requirement for a deformable collagenous matrix for the induction and maintenance of casein production. The mechanism by which extracellular matrix controls gene expression has not been investigated with MAC-T cells.

Hormone-responsiveness to prolactin is another characteristic of MAC-T cells. Exogenous prolactin augmented extracellular matrix signals by further increasing casein gene expression. This induction has a lag of at least 24 h with respect to β-casein mRNA abundance and 36 h for casein secretion. Prolactin effects observed in COMMA-D cells (Eisenstein, R. S. and Rosen, J. M. (1988) idem) show a similar pre-induction lag phase following addition of lactogenic hormones.

Lactose secretory function of the MAC-T cell line is comparable to freshly dissociated primary epithelial cells (Burwen, S. J. and Pitelka, D. (1980) idem). When plated on floating collagen gels in the presence of prolactin, lactose secretion in MAC-T cells range between 2–8 nmol/μg DNA/ 24 h compared to 4–12 nmol/μg DNA/24 h for primary cells. Omission of prolactin attenuates lactose secretion and led to a smaller accumulation of lactose in culture media. A suppression of lactose secretion as indicated by a plateau in media lactose concentration was noted after 48 h of prolactin stimulation and in the absence of prolactin. Similar findings by Burwen, S. J. and Pitelka, D. ((1980) idem) were interpreted as negative feedback regulation on lactose synthesis and secretion. Although the similarities in lactose secretory function between MAC-T and freshly dissociated mammary cells is encouraging, the absolute amount of lactose secreted is small relative to rates observed in vivo. A closer approximation of the in vivo hormonal milieu and a more complete extracellular matrix should improve this in vitro performance.

Example II

IN VITRO SCREENING FOR OPTIMIZING EUKARYOTIC EXPRESSION VECTORS

The current understanding of eukaryotic regulatory elements which regulate tissue specificity and activity of gene expression is inadequate. As such, large upstream fragments of DNA are typically used, in the hope of securing the necessary regulatory sequences (Gordon, K. et al., Bio/ Technology, (1987), 5:1183). Our poor capacity to predict promoter or enhancer activity places a premium on a screening system to evaluate the level of expression and tissue specificity of expression of DNA constructs. Transgenic mice represent the currently available screening method. These have not been entirely satisfactory due to obvious species differences. For example, a whey acid protein (WAP) is found in rodent milk but not ovine or bovine milk. Therefore, will the WAP promoter be effective for enhancing expression of bovine transgenes even if it is well expressed in mice. Similarly, will the WAP promoter confer tissue specificity for all species.

Established cell lines offer several advantages over transgenic rodent with regard to eukaryotic expression vector screening. They will permit the identification of potentially superior recombinant DNA constructs which can be used with confidence in the production of transgenic animals.

A typical example was recently presented by Doppler, W. et al., (PNAS (1989), 86:104). They examined the hormone responsive elements of the rat μ-casein gene which conferred sensitivity to prolactin and glucocorticoids. In this case, a mouse cell line, COMMA-D subclone HC II, was used to examine a 2300 base pair (bp) 5' flanking region for biological activity. Pools of HCll were transfected with various 5' deletions ranging from −2300 to +486 (with respect to transcription start site) and the induction of a reporter gene evaluated. The region of −285 to −170 bp was shown to contain strongly inducible promoter elements.

The example includes the following salient points:

1. Introduction of recombinant DNA constructs (vectors) into cells is easy and fast. This example used a calcium phosphate precipitation for DNA transfection, as we have with the MAC-T cells. The pSV-2neo/G418 selection protocol allows for rapid selection.
2. Clonal cell lines provide uniformity of biological systems between plates and between days of experiment. In this example, induction rates could be compared between all of the treatment groups because a clonal cell line was used. Variation is thereby kept to a minimum.
3. Large numbers of constructs could be tested in an economical way. Here, numerous 5' deletion mutants were tested in vitro to locate regulatory elements. The requirement for large numbers of tests was filled with this in vitro system.

This is important as each construct should be evaluated in several cells to obtain a representative expression. The integration of the construct into an area of the genome which is transcriptionally less active would present a false negative. Thus, several such experiments are needed to fully compensate for these "position effects".

Example III

FOREIGN GENE EXPRESSION

Eukaryotic fermentation is a viable means of overcoming the considerable problems associated with prokaryotic expression of mammalian proteins. Typically, eukaryotic expression of mammalian proteins. Typically, eukaryotic proteins require post-translational modification and the proper folding environment before they are active. An example of such production system was the synthesis of human tissue-type plasminogen activator (PA) within mouse cells reported by Integrated Genetics, now Genzyme (Reddy V. B. et al., DNA (1987) 6:461). Plasminogen activators are useful as therapeutic agents in thrombolysis. Reddy et al. (1987) created a recombinant DNA construct consisting of the human t-PA gene engineered into a mammalian expression vector. When this construct was transfected into mouse C127 cells, they produced large quantities of authentic human t-PA. This t-PA was immunologically and enzymatically similar to native human t-PA.

The benefits of such an approach are clear.

1. Appropriate recombinant DNA constructs can be transcribed/translated immediately in cell culture to produce authentic proteins. This gives flexibility to produce a large number of products or improve existing production systems.
2. Proteins of interest are secreted into the media where they can be removed. This permits large scale production via eukaryotic fermentation systems with continuous flow.

Example IV

MODIFIED MAC-T CELL LINE

To test the hypothesis that insulin-like growth factor-I (IGF-I) affects the growth of bovine mammary epithelial cells through an autocrine and/or paracrine pathway, a cell line (MD-IGF-I) was originated from MAC-T cells by cotransfection with a construct containing the cDNA for an ovine exon 2-encoded pre-pro-IGF-I under control of the mouse mammary tumor virus-long terminal repeat promoter. Clone MD-IGF-I contained multiple copies of the plasmid integrated into the genome, expressed the highest level of IGF-I mRNA, and secreted radioimmunoactive IGF-I into the medium. The mitogenic activity of MD-IGF-I cells was stimulated 80% by dexamethasone (DEX). The total DNA in MD-IGF-I cells was 2.5-fold higher than that in parental MAC-T cells in the presence of DEX. Conditioned medium from MD-IGF-I cells, induced with DEX, stimulated [$^3$H] thymidine incorporation into DNA of MAC-T cells and uninduced MD-IGF-I cells. These data provide evidence that IGF-I was secreted into medium by MD-IGF-I cells. It is suggested that IGF-I can stimulate the growth of mammary epithelial cells by an autocrine and/or paracrine mode of action. The MD-IGF-I cell line may be suitable system to study translational and posttranslational modifications of IGF-I peptides. (Molecular Endocrinology (1992) 6: 1774–1780).

MATERIALS AND METHODS

MMTV-LTR Plasmids

A 0.7-kb fragment encoding an exon 2 (previously exon 1A) prepro-IGF-I cDNA containing a 33-amino acid leader signal peptide was isolated from clone A21 by a BGIII restriction digest and purified from a low melting agarose gel using the Geneclean system™ (BIO 101, Inc., La Jolla, Calif.). The ends of the fragment were filled in using T4 DNA polymerase, generating blunt ends. The blunted oIGF-I insert was cloned into the SmaI site of the 7.6-kb expression vector pMSG (Pharmacia, LKB Biotechnology, Inc., Piscataway, N.J.). Thus, the oIGF-I cDNA was placed under the control of the MMTV-LTR promoter contained in the expression vector pMSG. To evaluate the activity of the MMTV promoter, bovine mammary epithelial MAC-T cells were transiently transfected with plasmid pMSC-CAT (Pharmacia).

Development of Stable MD-IGF-I Transformants

MAC-T cells were plated at a density of $2 \times 10^5$ in 60-mm tissue culture plates and cotransfected, using the calcium phosphate precipitation procedure, with the construct pMMTVIGF-I and a plasmid containing a cassette for resistance to HYG-B. Cells were glycerol shocked for 2 min at 37° C. After incubation for 48 h at 37° C., cells were placed in selective medium containing 200 µg/ml HYG-B (Sigma, St. Louis, Mo.). Resistant cells were selected after 14 days, and single cells were cloned by the limiting dilution procedure using 96-well plates. For Southern blot analysis, genomic DNA was extracted, digested with EcoRI, and run on 1% agarose gels. The Southern blot was probed with a 0.7-kb oIGF-I cDNA labeled by nick translation.

Northern Analysis

MD-IGF-I clones were plated in 100-mm tissue culture plates in DMEM-10% FCS with 200 µg/ml HYG-B. When cells were at 85% confluency, medium was removed, and cells were washed with Dulbecco's PBS. Then, fresh DMEM medium containing 0.1 µM DEX to induce the MMTV-LTR promoter was added. Cells were trypsinized after 24 h, and total RNA was extracted using a guanidinium, thiocyanate isolation procedure and separated on a 1% agarose gel containing 2.2M formaldehyde. Northern blots (Nitroplus, MSI, Inc., Westborough, Mass.) were hybridized overnight at 42° C. and washed at high stringency according to the manufacturer's instruction (MSI).

Growth of MD-IGF-I Cells and Detection of IGF-I in Medium

A series of experiments was designed to monitor the mitogenic activity of the MD-IGF-I cell line. For all growth experiments, MD-IGF-I and control MAC-T cells were plated at a density of $2 \times 10^4$ cells in 24-well tissue culture plates in DMEM with 10% FCS. After 24 h, medium was removed, and cells were washed with PBS. In a first experiment, the test medium was DMEM without FCS, but with or without 200 µg/ml HYG-B and with or without 0.0, 0.1, and 2.5 µM DEX. Cells were collected 24, 48 and 72 h after induction with DEX, and total DNA per well was measured. Six replicates were collected for each treatment, and samples were assayed in duplicate. To test the sensitivity over time of the MD-IGF-I cells to induction with DEX, cells were induced with 0.1 and 2.5 µM DEX up to 240 h. At the end of each treatment, cells were harvested for determination of total DNA.

The growth response of MD-IGF-I cells to exogenous human IGF-I (100 ng/ml; Boehringer Mannheim, Indianapolis, Ind.) was ascertained in the presence or absence of 0.1 µM DEX. Cells were harvested after 72 h, and total DNA was used as an indicator of mitogenic activity.

To confirm the secretion of biologically active IGF-I in condition medium of MD-IGF-I cells, $5 \times 10^5$ MD-IGF-I and MAC-T cells were plated in 100-mm tissue culture plates for 72 h in the presence and absence of 0.1 µM DEX. At the end of the conditioning period, medium from each treatment was collected and used to culture MAC-T or MD-IGF-I cells, seeded in 24-well culture plates. After 16 h, cells were pulsed for 2 h with [$^3$H]thymidine (ICN Biomedicals, Inc., Costa Mesa, Calif.), and incorporation was measured, as previously described. The presence of IGF-I in the medium was measured by a previously validated RIA procedure. Medium was subjected to methanol-formic acid extraction to correct for possible false positive results due to IGF-binding proteins. After extraction, the amount of IGF-I associated with BPs in control serum samples was 8.0%, which confirmed that minimal amounts of BPs remained in the samples tested by RIA. The RIA intraassay coefficient of variation in control serum samples was less than 10%.

Results

Figure 2:
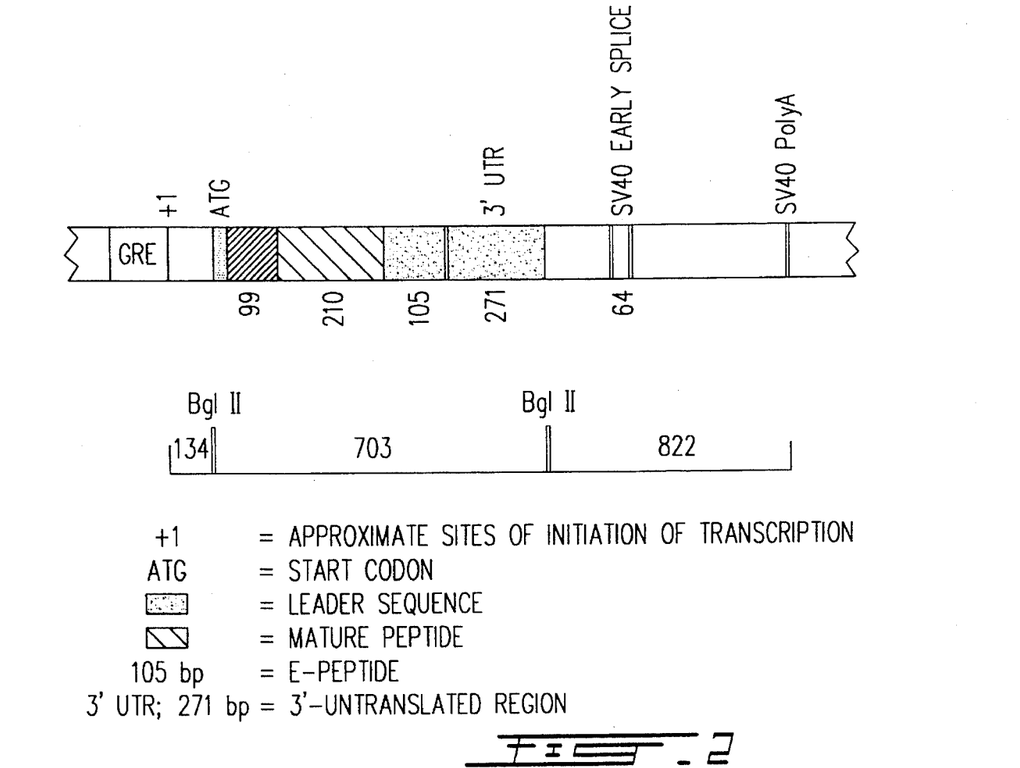
FIG. 2 is a restriction map of pMSG.

An exon 2-containing oIGF-I cDNA, encoding a 33-amino acid leader peptide, was cloned into expression vector pMSG. The resulting plasmid, designated pMMTV-IGF-I (MMTV, mouse mammary tumor virus), contained the oIGF-I cDNA under the control of the MMTV-long terminal repeat (MMTV-LTR) promoter (FIG. 2). Expression vector pMMTV-IGF-I contained a transcription initiation site 134 basepairs (bp) up-stream and a simian virus-40 (SV40) polyadenylation site 822 bp down-stream of the closed oIGF-I cDNA. Thus, the predicted length of the oIGF-I transcript from pMMTV-IGF-I was approximately 1.65 kilobases (kb). The MMTV-LTR promoter was shown to be active and inducible by dexamethasone (DEX) in the bovine mammary epithelial cell line MAC-T after transient transfection studies with plasmid pMSG-CAT.

Stable MAC-T transformants containing pMMTV-IGF-I were isolated in Dulbecco's Modified Eagle's Medium (DMEM) plus hygromycin-B (HYG-B) after cotransformation with a plasmid conferring HYG-B resistance. The presence of integrated copies of pMMTV-IGF-I was confirmed by Southern blotting. Stable transformants contained single or multiple copies of pMMTV-IGF-I. One clone, MD-IFG-I, contained approximately 30 copies of pMMTV-IGF-I integrated in a tandem array and was used for further analysis.

Figure 3A:
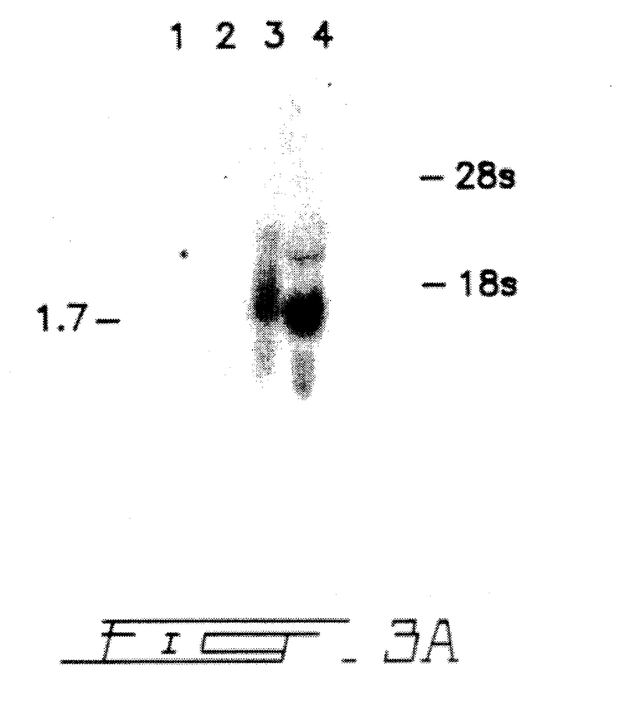
FIGS. 3A–3B is a Northern blot of total RNA from MAC-T and MD-IGF-I cells.
Figure 3B:
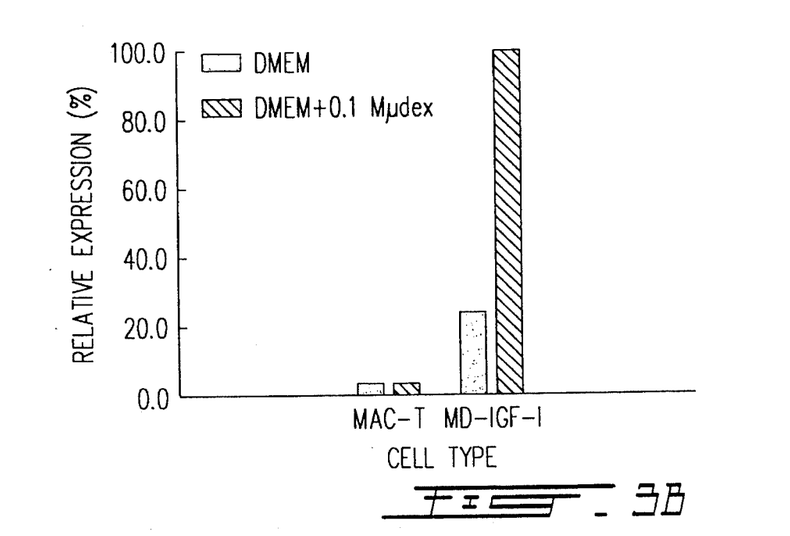

Northern blot of total RNA extracted from MAC-T and MD-IGF-I cells showed (FIG. 3) that a RNA species of approximately 1.7 kb hybridized strongly when the MD-IGF-I cells were induced with DEX. The length of his transcript is in agreement with the predicted size of processed mRNAs transcribed from pMMTV-IGF-I. Densitometric analysis of autoradiograms showed a 40-fold increase in the intensity of hybridizing RNA species compared to that in MAC-T cells. Even in the absence of DEX, MD-IGF-I cells demonstrated detectable quantities of this RNA species.

Example V

IMMORTALIZED RUMINANT CELL LINE

Primary mammary gland cells are obtained by aseptic biopsy from lactating French Alpine goats at slaughter and dissociated as described by Burwen, S. J. and Pitelka, D. (Exp. Cell. Res. (1980) 126:249). Mammary tissue is minced, placed in a trypsinizing flask to which is added 1:10 (w/v) dissociation media (1×Hank's Buffered Saline solution, 11 mM glucose, 4% bovine serum albumin and collagenase 200 IU/ml) and rotated at 200 rpm for 60 min at 37° C. Single primary cells obtained by filtration through 150 µm Nitex™ screens are washed with Dulbecco's phosphate buffered saline (DPBS) and grown in Dulbecco's Modified Eagles Media (DMEM), 20% fetal calf serum (FCS), 5 µg/ml insulin, 1 µg/ml hydrocortisone, 100 IU/ml penicillin and 100 µg/ml streptomycin on tissue culture plastic with 5% $CO_2$ and 100% humidity at 37° C.

The mixed cell population is transfected using adherent cells ($1.0 \times 10^5/cm^2$) using 10 µg pBAPSV40TtsA58 and 1 µg pSV2-neo per $1 \times 10^7$ cells via the calcium phosphate procedure of Graham, F. L. and van der Eb, A. J. (Virol. (1973) 52:456). After 4 h of transfection, the cells are washed once with DPBS and glycerol shocked for 2 min, washed with DPBS and complete media added for 24 h. Cells are then trypsinized and plated in 6 well multiplates ($5.2 \times 10^3$ cells/$cm^2$) in complete media with 400 µg/ml Geneticin®.

Surviving colonies are examined morphologically to identify epithelial-like cells; showing a round shape with no cytoplasmic projections and a high cytoplasmic to nuclear area ratio. Fifteen of these colonies are cloned using cloning rings and then expanded by subsequent cultivation in 96 well plates, 12 well and then 6 well plates. Confirmation of an epithelial origin is obtained via indirect immunofluorescence. Monoclonal antibodies (MAb) which react with cytokeratin (Jahn, L. et al., Differentiation (1987) 36:234; type II, subfamily No 1-8) and vimentin (Jahn, L. et al. (1987) idem) are used to characterize cell type as epithelial or stromal, respectively. When cells are grown on eight well chamber slides (plastic substrata), fixation and staining can be completed directly using manufacturers recommendations. Cells on collagen are briefly treated with collagenase and then plated on plastic for 30 min prior to staining. Immunofluorescent localization of the primary antibody is accomplished using a second antibody, goat anti-mouse Ig-FITC conjugate. Positive biological control for cytokeratin staining are the BMGE cells, which show a characteristic epithelial pattern (Schmid, E. et al. (1983) idem). Incubation of cells with FITC-goat anti-mouse IgG alone failed to result in cell staining.

Samples are directly visualized with a Jenalumar microscope, at 400× magnification, equipped with epifluorescence optics and appropriate excitory and barrier filters for FITC. Establishment characteristics To identify cloned cells which are established but not transformed, the following criteria are used: 1) continuous passage without crisis for >70 passages; 2) expression of the large T antigen; and 3) lack of tumorigenicity in immunodeficient mice. Continuous growth of cells is evaluated as the cells are passaged 1:4 over time and the population doubling time is measured. Expression of the large T antigen is evaluated by Western blotting using the monoclonal antibody to SV40 large T antigen (provided by G. Matlashewski, McGill University, Montreal, Canada). This monoclonal antibody is used at a dilution of 1:2.

Tumorigenicity is evaluated by injecting $5 \times 10^6$ cells/100 µl DPBS subcutaneously into 28–40 day-old Nu/Nu CD-1 homozygous mice (Charles River Inc.). As a positive control P160 cells are also injected ($5 \times 10^5$ cells/100 µl) at a different site. Mice are palpated for the presence of tumors after 8 weeks. Growth in soft agar is evaluated by placing 600 cell/ml on 0.3% agarose in complete media. Any colonies present after 16 days are counted.

This series of experiments create and characterize a series of caprine mammary epithelial cell lines which are established in culture. Such cell lines may be useful in examining the level of expression of foreign DNA expression constructs destined for use in the creation of transgenic goats.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. An immortalized ruminant mammary epithelial cell line prepared by the transfection of primary ruminant mammary epithelial cells with the SV40 large T antigen gene, wherein said mammary epithelial cells are selected from goat and sheep cells, said cell line having normal physiological responses such that, under hormonal stimulation, milk constituents comprising α- and β-casein and lactose are produced.

2. An immortalized ruminant mammary epithelial cell line according to claim 1, wherein said cell line is transfected with a suitable DNA expression vector to express a gene product.

3. A method of stimulating the production of certain milk proteins in mammary epithelial cells in vitro which comprises the steps of:

a) incubating the immortalized ruminant cell line of claim 1 in a culture medium;

b) adding to the culture medium one or more lactation hormones to stimulate production of certain milk proteins by said cell line; and c) measuring the amount of α- and β-casein and lactose produced and secreted into the culture medium by said cell line.

4. A method of in vitro screening for foreign gene expression in ruminants which comprises the steps of:

a) providing the immortalized cell line of claim 1 in a culture medium;

b) transfecting the cells of step a) with a foreign DNA construct comprising a promoter and a gene wherein the mammary gland is the target organ for said gene expression; and c) assaying at least one of the transfected cells or media of step b) for said foreign gene expression; thereby testing the suitability of the foreign DNA construct prior to making a transgenic ruminant animal.

5. A method according to claim 4, wherein the foreign DNA construct comprises a gene selected from the group consisting of human neuropeptide Y, yeast peroxisomal catalase, flounder antifreeze protein, human ferritin, human tissue plasminogen activator, β-galactosidase, insulin-like growth factor, large T antigen, aminoglycoside phosphotransferase and hygromycin B phosphotransferase.

* * * * *